United States Patent
Mendel et al.

(10) Patent No.: US 11,938,155 B1
(45) Date of Patent: Mar. 26, 2024

(54) COMPOSITIONS CONTAINING HONEY AND LANOLIN

(71) Applicants: Abbie Beth Mendel, Las Vegas, NV (US); Gerard Edouard Mendel, Las Vegas, NV (US)

(72) Inventors: Abbie Beth Mendel, Las Vegas, NV (US); Gerard Edouard Mendel, Las Vegas, NV (US)

(*) Notice: Subject to any disclaimer, the term of this patent is extended or adjusted under 35 U.S.C. 154(b) by 0 days.

(21) Appl. No.: 18/475,217

(22) Filed: Sep. 27, 2023

(51) Int. Cl.
| | |
|---|---|
| A61K 36/00 | (2006.01) |
| A61K 31/355 | (2006.01) |
| A61K 35/12 | (2015.01) |
| A61K 35/644 | (2015.01) |
| A61K 36/886 | (2006.01) |
| A61K 47/44 | (2017.01) |
| A61P 17/00 | (2006.01) |
| A61P 17/02 | (2006.01) |
| A61P 17/04 | (2006.01) |
| A61P 17/10 | (2006.01) |
| A61P 31/10 | (2006.01) |

(52) U.S. Cl.
CPC .......... *A61K 35/644* (2013.01); *A61K 31/355* (2013.01); *A61K 35/12* (2013.01); *A61K 36/886* (2013.01); *A61K 47/44* (2013.01); *A61P 17/00* (2018.01); *A61P 17/02* (2018.01); *A61P 17/04* (2018.01); *A61P 17/10* (2018.01); *A61P 31/10* (2018.01)

(58) Field of Classification Search
None
See application file for complete search history.

(56) References Cited

U.S. PATENT DOCUMENTS

| | | | | |
|---|---|---|---|---|
| 6,482,442 B1 * | 11/2002 | Dado | ...... | A61P 17/02 424/539 |
| 2007/0098671 A1 * | 5/2007 | Martin | ...... | A61K 36/886 424/539 |
| 2011/0135746 A1 * | 6/2011 | Triplett | ...... | A61K 35/644 424/537 |

* cited by examiner

*Primary Examiner* — Russell G Fiebig
(74) *Attorney, Agent, or Firm* — Sam Pierce

(57) ABSTRACT

According to an aspect of the present invention, there are provided compositions, comprising: 47.5% to 52.5% unfiltered honey by volume; 22.5% to 27.5% natural lanolin by volume; 10.0% to 15.0% melted beeswax by volume; 5.0% to 7.5% pure aloe by volume; 1.5% to 2.5% pure Vitamin E by volume; and 3.0% to 5.0% Peppermint oil, Lavender oil, or cinnamon by volume.

9 Claims, 1 Drawing Sheet

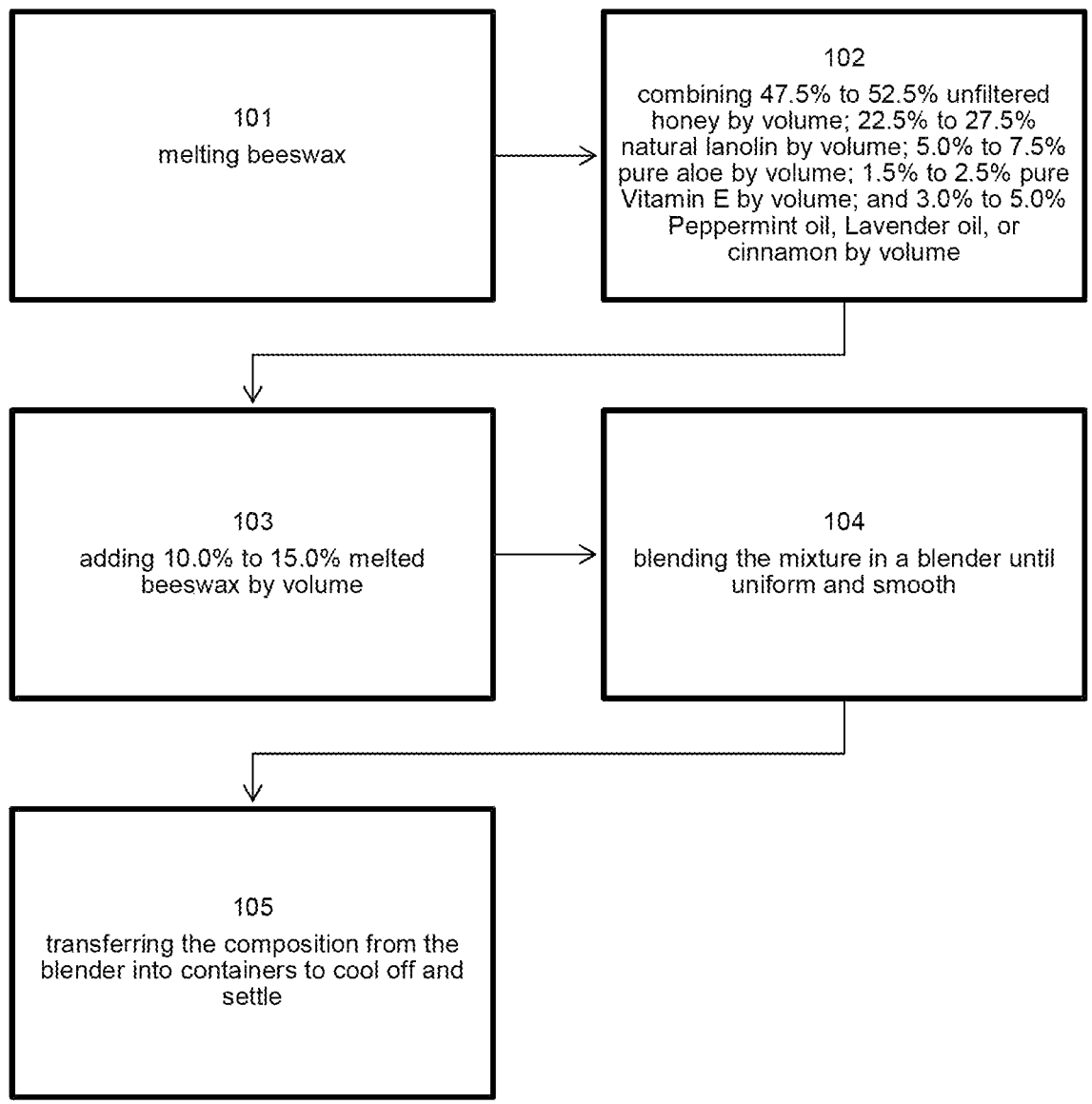

COMPOSITIONS CONTAINING HONEY AND LANOLIN

BACKGROUND

People have known for thousands of years that raw honey has many medicinal properties such as wound healing and antibacterial activity. Honey was widely used for medicinal purposes in the ancient world and is still common in Africa, India and the Middle East. However, despite extensive research, the healing properties of honey have not yet been fully elucidated.

Most honeys are in some way antibacterial, some more than others. Honey with high antibacterial activity, typically has high levels of hydrogen peroxide ($H_2O_2$) which is referred to as "peroxide activity" (PA). Other properties of honey commonly known to underpin its antibacterial activity are low pH and high sugar content (high osmotic effect). It is likely that the historical use of honey as a wound healing agent stems from its antibacterial activity.

The PA activity of honey is derived from an enzyme called glucose oxidase. Like many enzymes, glucose oxidase is inactivated by light and heat. The stronger the light and/or heat, the faster it is inactivated. Room temperature and low light, given enough time, will also reduce the glucose oxidase activity. Glucose oxidase only becomes active when honey is diluted. The precise reasons for the activation of the enzyme upon dilution are still not clearly known.

Two honeys, known as jelly bush and manuka honey, are interesting because they can have anti-microbial activity due to some property other than the production of hydrogen peroxide, low pH or high sugar content. Both jelly bush and manuka are plants that are *Leptospermum* species. The antibacterial activity of these honeys is referred to as the non-peroxide activity (NPA). Unlike PA, NPA is stable to moderate heat, light and even gamma radiation.

Honey is a complex, naturally occurring, mixture of components. After processing of the collected nectar by bees (including addition of various components one of the most important of which is diastase), the water content of the modified nectar evaporates slowly from about 70 to 80% by weight, to about 17 to 18% by weight, eventually providing ripe honey. Ripe honey, therefore, has a low water activity, which contributes to its high osmotic effect and therefore its antibacterial activity.

Direct application of unadulterated honey to, for example, a site of injury, can be difficult because of honey's inherent properties such as varying viscosity and natural "stickiness". Use of unadulterated honey can also be time consuming, messy and impractical.

Lanolin is the unctuous secretion of the sebaceous glands of sheep which is deposited onto the wool fibers. It softens the fleece and serves to protect the fleece against the elements. It is a wax, not a fat. It is a complex mixture of esters, di-esters and hydroxy esters of high molecular weight lanolin alcohols (69 aliphatic alcohols (C12-C36) and 6 sterols have been identified in lanolin) and high molecular weight lanolin acids (approximately 138 acids (C7-C41) have been identified in lanolin). Lanolin is a by-product of the wool-scouring industry.

Wool grease constitutes 10-15% of the weight of sheared wool, depending on the breed of sheep, anatomical area sheared, inner and outer fleece, and season. The average composition of Australian fleeces is 11-16% grease, 6-8% suint (potassium salts of various organic and inorganic acids in the sweat), 10-12% water, 8-19% dirt and 49-61% wool fiber. One hundred pounds of wool yield about 2 to 4 pounds of lanolin. Lanolin is recovered by wool-scouring, followed by separation and purification which may include acid cracking or centrifugal washing, neutralization, removal of soaps, filtration, bleaching and deodorization.

Lanolin is an effective emollient, which by subjective evaluation, effects softening and improvement of dry or rough skin caused by lack of sufficient natural moisture retention. Lanolin is not however satisfactory as a skin treatment product because of its high viscosity, tackiness, and high drag property, thereby making it aesthetically unacceptable to consumers and too difficult to spread onto the skin to be widely accepted.

While honey and lanolin are both known to have desirable properties for topical application on the body of a person, improved compositions which address some of the shortcomings described and other limitations are desirable.

SUMMARY OF INVENTION

Therefore, an aspect of the present invention provides a composition comprising 47.5% to 52.5% unfiltered honey by volume; 22.5% to 27.5% natural lanolin by volume; 10.0% to 15.0% melted beeswax by volume; 5.0% to 7.5% pure aloe by volume; 1.5% to 2.5% pure Vitamin E by volume; and 3.0% to 5.0% Peppermint oil by volume.

Another aspect of the present invention provides a composition comprising 47.5% to 52.5% unfiltered honey by volume; 22.5% to 27.5% natural lanolin by volume; 10.0% to 15.0% melted beeswax by volume; 5.0% to 7.5% pure aloe by volume; 1.5% to 2.5% pure Vitamin E by volume; and 3.0% to 5.0% Lavender oil by volume.

BRIEF DESCRIPTION OF THE DRAWING

FIG. 1 illustrates a flow diagram for preparation of a composition according to an embodiment.

DETAILED DESCRIPTION

Compositions containing honey and lanolin are described. BeesWax is also an important ingredient as well. The main ingredients are Honey, Lanolin, and BeesWax. The aloe, vitamin e & scented oils are the carrier oils and provide support for the main ingredients. The secondary ingredients "boost" the main ingredients, making them more effective.

FIG. 1 illustrates a flow diagram for preparation of a composition according to an embodiment.

Step 101 is melting beeswax.

Step 102 is combining 47.5% to 52.5% unfiltered honey by volume; 22.5% to 27.5% natural lanolin by volume; 5.0% to 7.5% pure aloe by volume; 1.5% to 2.5% pure Vitamin E by volume; and 3.0% to 5.0% Peppermint oil, Lavender oil, or cinnamon by volume.

Step 103 is adding 10.0% to 15.0% melted beeswax by volume.

Step 104 is blending the mixture in a blender until uniform and smooth.

Step 105 is transferring the composition from the blender into containers to cool off and settle.

Development of the compositions of embodiments will now be described.

Formula Progressions

Composition 1
- 3 oz Honey
- 2 oz lanolin
- 2 oz aloe
- 1 oz water
- 1 oz Vitamin E Oil After mixing the above composition, the mixture was very watery. An added an additional part (oz) of honey was added to thicken up the mixture.

Results

The mixture was far too oily. Oil was separating from mixture (most likely due to the presence of water and aloe). It was decided to try a composition without water to see if a better texture and mixture could be obtained.

Composition 2
- 5 oz Honey
- 2 oz Aloe
- 1 oz Vitamin E
- 2 oz lanolin

Results

The mixture was still far too oily. The texture was not suitable. The smell of the lanolin was strong. It was decided to add an ingredient that helps with the smell. The ingredient must have therapeutic benefits for skin—not just a smell benefit. Every ingredient must have skin healing benefits to be included in the formula.

It was discovered that peppermint oil has skin healing properties and given the strong minty smell of peppermint, it was decided to test it to see if it can mask the smell of the lanolin.

The lanolin was heated to make the mixture smoother because the texture has been unsuitable.

Composition 3
- 4 oz honey
- 2 oz Aloe
- 1 oz Vitamin E
- 2 oz Lanolin
- 1 oz beeswax
- 0.167 oz peppermint oil

Results

The lanolin was not heated. Beeswax was added and heated to melt the beeswax. It was hoped this would thicken the mixture. Also, the healing properties of beeswax were desirable. With previous compositions, mixing was done by hand. This time, a small mixer was used to try to get a smoother texture.

The peppermint oil was a useful addition. It has healing properties and masks the lanolin smell well. A nice refreshing "candy cane" smell was obtained.

It was decided to try Lavender as well. It was contemplated that peppermint would be a daytime "refreshing" formula and Lavender would be a nighttime "calming" formula.

The texture still was not suitable. Beeswax was cooling off in a "chunky" manner, leaving the texture full of lumps from the wax. Some separation of oil from mixture was observed when the mixture sits.

Though the texture was not satisfactory, the composition was proving useful for different skin issues. For example, the composition was able to stop the itch associated with a bug bite, and the bite was gone without a trace within a few hours.

Composition 4
- 4 oz Honey
- 2 oz Lanolin
- 1 oz Beeswax
- 2 oz Aloe
- 1 oz Vitamin E
- 0.333 oz Peppermint Oil or Lavender Oil

Results

The texture was still unsatisfactory because the beeswax was not smoothing out enough. However, the composition could still be used.

It was tested whether there were any negative effects of the mixture for example, that skin dries out, get irritated, inflammation, etc.

Zero negative effects were observed. Skin continued to improve, not lose moisture, and no side effects, pain, inflammation, or any other adverse effects were observed.

If the composition was placed too close to the eyes, the "vapors" of the peppermint were felt by the eye. No irritation occurred, but the peppermint "vapors" were felt when the composition was placed directly near the eye. It was considered that the composition should not be placed near the eyes.

Scars, cuts, bug bites, toe fungus, eczema, acne, dried skin, blemishes, and rashes among other conditions were tested to see if the composition would be effective in providing relief, and the results were positive.

Composition 5
- 4 oz Honey
- 2 oz Lanolin
- 1 oz Beeswax
- 2 oz Aloe
- 0.5 oz Vitamin E
- 0.333 oz Peppermint Oil or Lavender Oil

Results

The texture was still unsatisfactory and it was considered how to get it smooth and creamy. The oil is still separating from the mixture, which is not satisfactory. A next set of tests is varying the Aloe amount was planned, as Aloe is a water-based ingredient which is most likely causing the oil separation. The composition was still too oily, and it was considered that removing or lessening the percentage of Aloe to fix the texture would worsen this issue.

Composition 6
- 4 oz Honey
- 2 oz Lanolin
- 1 oz Beeswax
- 0.5 oz Aloe
- 0.167 oz Vitamin E
- 0.333 oz Peppermint Oil or Lavender Oil or Cinnamon Bark Oil

Results

The amount of Aloe and Vitamin E was reduced. This change resulted in a satisfactory texture which is smooth and the correct thickness.

The embodiments described above are given merely for example and for the purpose of facilitating the understanding of the present invention and are not intended to limit the interpretation of the present invention. The respective elements and their arrangements, materials, conditions, shapes, sizes, or the like of the embodiment are not limited to the illustrated examples but may be appropriately changed. Further, the constituents described in the embodiment may be partially replaced or combined together.

What is claimed is:

1. A topical balm, comprising:
   47.5% to 52.5% unfiltered honey by volume;
   22.5% to 27.5% natural lanolin by volume;
   10.0% to 15.0% melted beeswax by volume;
   5.0% to 7.5% pure aloe by volume;
   1.5% to 2.5% pure Vitamin E by volume; and
   3.0% to 5.0% scented oil by volume.

2. The topical balm of claim 1, wherein the scented oil is peppermint oil.

3. The topical balm of claim 1, wherein the scented oil is lavender oil.

4. The topical balm of claim 1, wherein the scented oil is cinnamon bark oil.

5. The topical balm of claim 1, wherein the composition is applied to an external epidermal surface of a person.

6. The topical balm of claim 5, wherein the composition is applied to lips of a person.

7. The topical balm of claim 5, wherein the application treats one or more of scars, cuts, bug bites, toe fungus, eczema, acne, dried skin, blemishes, and rashes.

8. A method of preparing a topical balm, comprising:
   melting beeswax;
   combining 47.5% to 52.5% unfiltered honey by volume; 22.5% to 27.5% natural lanolin by volume; 5.0% to 7.5% pure aloe by volume; 1.5% to 2.5% pure Vitamin E by volume; and 3.0% to 5.0% scented oil by volume;
   adding 10.0% to 15.0% melted beeswax by volume; and
   blending the mixture in a blender until uniform and smooth.

9. The method of claim 8, further comprising transferring the topical balm from the blender into containers to cool off and settle.

* * * * *